(12) United States Patent
Bende et al.

(10) Patent No.: US 9,500,578 B2
(45) Date of Patent: Nov. 22, 2016

(54) METHOD AND DEVICE FOR CORROSION TESTING OF SOLAR CELLS

(71) Applicant: Stichting Energieonderzoek Centrum Nederland, Petten (NL)

(72) Inventors: Evert Eugene Bende, Petten (NL); Bas Bernardus van Aken, Petten (NL); Willemina Eerenstein, Petten (NL); Robert Jan Gouwen, Petten (NL)

(73) Assignee: STICHTING ENERGIEONDERZOEK CENTRUM NEDERLAND, Petten (NL)

( * ) Notice: Subject to any disclaimer, the term of this patent is extended or adjusted under 35 U.S.C. 154(b) by 0 days.

(21) Appl. No.: 14/762,540

(22) PCT Filed: Jan. 21, 2014

(86) PCT No.: PCT/NL2014/050027
§ 371 (c)(1),
(2) Date: Jul. 22, 2015

(87) PCT Pub. No.: WO2014/116107
PCT Pub. Date: Jul. 31, 2014

(65) Prior Publication Data
US 2015/0362424 A1 Dec. 17, 2015

(30) Foreign Application Priority Data
Jan. 22, 2013 (NL) ..................................... 2010161

(51) Int. Cl.
*G01N 17/02* (2006.01)
(52) U.S. Cl.
CPC ..................................... *G01N 17/02* (2013.01)

(58) Field of Classification Search
CPC .............................. G01N 17/02; G01N 17/04
See application file for complete search history.

(56) References Cited

U.S. PATENT DOCUMENTS

| 6,611,151 B1* | 8/2003 | Ruedisueli | G01N 17/02 324/700 |
| 2013/0005071 A1* | 1/2013 | Hiraike | B29C 65/02 438/73 |

OTHER PUBLICATIONS

Electrochemical Noise From Wikipedia, 1 page.
Gonzalez-Nunez, M.A., et al; R/S Fractal Analysis of Electrochemical Noise Signals of Three Organic Coating Samples Under Corrosion Conditions; The Journal of Corrosion Science and Engineering; vol. 6, Paper C117, Jul. 2003.
Greisiger, H., et al; On the Interpretation of the Electrochemical Noise Data for Coatings; Progress in Organic Coatings, vol. 39, pp. 31-36, 2000.
Zahner-Elektrik Gmbh & Co. KG, Noise, Apr. 2012.
Zahner-Elektrik Gmbh & Co. KG, Advances in Electrochemical Applications of Impedance Spectroscopy, Jul. 1996, 5 pages.

* cited by examiner

*Primary Examiner* — Jennifer Dieterle
(74) *Attorney, Agent, or Firm* — Jackson Walker LLP

(57) ABSTRACT

Corrosion effects in a solar cell are measured by means of a conduit with electrolytic fluid. The rim of an open end of the conduit is placed against the surface of the solar cell to expose a selected area of the solar cell to the electrolytic fluid, leaving a free part of the planar surface of the solar cell outside the exposed area. Current and/or voltage fluctuations are measured in an electric circuit that contains the electrolytic fluid, an interface between the electrolytic fluid on the exposed area and a conductor layer on the planar surface, and a contact to the conductor layer in the free part.

20 Claims, 4 Drawing Sheets

METHOD AND DEVICE FOR CORROSION TESTING OF SOLAR CELLS

FIELD OF THE INVENTION

The invention relates to a method and device for testing solar cells.

BACKGROUND

A solar cell contains a semi-conductor structure and metallization on surface areas of the structure, to transmit an electric potential difference between the areas that arises from conversion of light in the semi-conductor structure. The operational lifetime of the solar cell depends on the susceptibility of the solar cell to corrosion when it is exposed to various weather conditions. To optimize the operational lifetime it is desirable to measure the susceptibility to corrosion.

Electrochemical noise (ECN) measurements are a known method to test materials for susceptibility to corrosion. Known ECN measurements comprise measurement of noise properties of the spontaneous electric current through a connection between electrodes made of the material under test, when the electrodes are immersed in an electrolyte bath. ECN measurements may also comprise measurement of noise properties of spontaneous electric voltage between the electrodes, or between an electrode made of the material under test and a reference electrode.

The material that is used for metallization of solar cells could per se be tested by means of ECN measurements. However, it has been found that this does not give a reliable prediction of the effect of susceptibility to corrosion on the operational lifetime. The geometric properties of the metallization, such as its thickness and layout, and the way in which the material is applied have been found to affect the operational lifetime.

The inventors propose to apply ECN measurements to solar cells with metallization to test the susceptibility of the metallization of solar cells to corrosion. Conventional ECN measurements can be applied to solar cells by immersing solar cells in an electrolyte bath and measuring currents through the metallization into the bath and/or voltages on the metallization. However, it has been found these measurements are affected by active behavior of the solar cells, such as photo-currents.

SUMMARY

It is an object to provide for a method of testing solar cells in a way in which an effect of active behavior of the solar cell on the test can be controlled.

A method of measuring corrosion effects in a solar cell is provided, comprising
  keeping a planar surface of the solar cell and a rim of an open end of a conduit directly or indirectly pressed against each other, the conduit comprising electrolytic fluid, whereby an exposed area of the solar cell that is encircled by the open end of the conduit is exposed to the electrolytic fluid, leaving a free part of the planar surface of the solar cell extending beyond said exposed area unexposed;
  measuring current and/or voltage fluctuations in an electric circuit that contains the electrolytic fluid, an interface between the electrolytic fluid on the exposed area and a conductor layer on the planar surface, and a contact to the conductor layer.

Herein, a conduit is used to expose a conductor layer on a planar surface of the solar cell locally to electrolytic fluid. In this way effects of the active behavior on the fluctuation measurements can be controlled. When the conductor layer is a patterned layer, such as a set of conductor lines, selected parts of the layer can be exposed to perform location selective measurement. In an embodiment a sealing ring is pressed between the planar surface and the open end of the conduit. The contact of the electric measuring circuit to the conductor layer may be made on a free part of the conductor layer on the planar surface that extends beyond the exposed area. The use of a limited exposed area makes it possible to use such a contact. In another embodiment, the contact may be made on an opposite planar surface of the solar cell, through a via between the planar surfaces of the solar cell. This is made possible because the exposed area is localized on one planar surface. In an embodiment the conductor layer entirely covers said planar surface. In an embodiment the conductor is directly exposed to the electrolytic fluid. In an embodiment at least the conductor layer on said exposed area is covered by a protective electrically insulating layer.

A further solar cell may be in contact with the electrolytic fluid in the conduit and fluctuations of current from a contact on that further solar cell to the contact on the solar cell may be measured. The solar cells may have identical structure, i.e. they may be made of the same semiconductor material with the same layers in or on that semiconductor material and the same patterns of layers. This facilitates determination of the effects of external conditions like illumination and/or temperature differences. Alternatively, solar cells with different structure may be used. This makes it possible to determine the effects of the structure. This makes it possible to compare corrosion of the solar cells.

In an embodiment the solar cell and the further solar cell have mutually different structure. In another embodiment the solar cell and the further solar cell have identical structure. In an embodiment the arrangement of the further solar cell in conjunction with the conduit may be similar to that of the first mentioned solar cell. For example the exposed areas may have the same size. This facilitates the comparison.

In an embodiment voltage fluctuations of a voltage between the contact and an electrode in the electrolytic fluid in the conduit are measured. These voltage fluctuations may be measured simultaneously with fluctuations in the current through the contact to the solar cell.

In an embodiment a bias voltage is applied between the conductor layer and an electrode in the electrolytic fluid. This makes it possible to measure the effect of simulated photovoltaic voltages from a series arrangement of solar cells. In a further embodiment the electrode in the electrolytic fluid is covered with a glass layer. This makes it possible to simulate the effect of a glass cover on the solar cells on corrosion.

In an embodiment the planar surface in the exposed area with light through the conduit during at least part of said measuring of current and/or voltage fluctuations. This makes it possible to measure the effect of lighting. In a further embodiment, the intensity of a light source is varied and results from the measurements of the current and/or voltage fluctuations, such as noise parameters are determined in synchronism with variation of the light intensity. This makes it possible to perform more accurate measurements of the effect of lighting. In an embodiment the back surface of the solar cell may be lighted as well to determine the effect of lighting that surface.

In an embodiment values of a statistical property may be determined from positive and negative current and/or voltage fluctuations respectively and comparing the values of the statistical property.

A measuring system for measuring corrosion effects in a solar cell is provided, the system comprising
a conduit comprising electrolytic fluid;
a solar cell having a planar surface, the solar cell comprising a conductor layer on the planar surface and a contact to the conductor layer, a rim of the conduit at an open end of the conduit being directly or indirectly in contact with the planar surface, whereby an exposed area of the solar cell that is encircled by the open end of the conduit is exposed to the electrolytic fluid, leaving a free part of the planar surface of the solar cell extending beyond said exposed area unexposed;
an electric measuring device with a first terminal connected to the contact and a second terminal coupled to the electrolytic fluid in the conduit, the electric measuring being configured to measure current and/or voltage fluctuations between the first and second terminal.

In a further embodiment, the measuring system comprises
a further solar cell having a further planar surface, a further conductor layer on the planar surface and a further contact on the further conductor layer, a further open end of the conduit being directly or indirectly in contact with the further planar surface, whereby a further exposed area of the further solar cell that is encircled by the further end of the conduit is exposed to the electrolytic fluid,
the second terminal of the electric measuring device being connected to the further contact.

A measuring system is provided to perform the method.

BRIEF DESCRIPTION OF THE DRAWING

These and other objects and advantageous aspects will become apparent from a description of exemplary embodiments by reference to the following figures

DETAILED DESCRIPTION OF EXEMPLARY EMBODIMENTS

Figure 1:
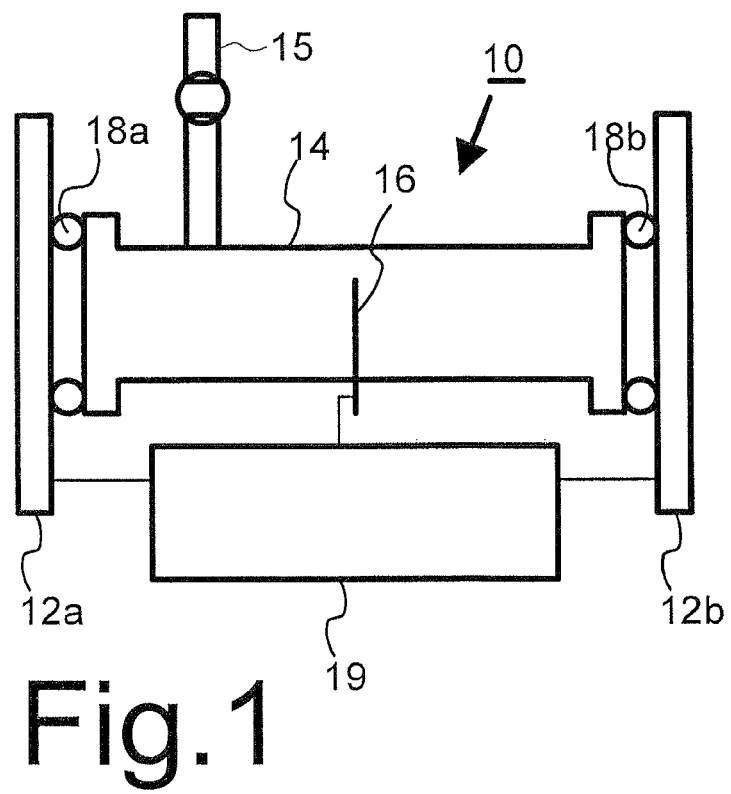
FIG. 1 shows an electrochemical noise measuring device

FIG. 1 shows an electrochemical noise measuring device 10 attached to a first and second sample solar cell 12a,b. Electrochemical noise measuring device 10 comprises a conduit 14 of electrically insulating material, filled with electrolyte fluid, an electrode 16 in conduit 14, sealing rings 18a,b at first and second ends of conduit 14 and an electronic measuring circuit 19 with a first terminal coupled to electrode 16 and second and third terminals coupled to conductors on first and second sample solar cell 12a,b respectively. Conduit 14 has one or more inlets and/or outlets 15 (only one shown) for letting in and/or removing electrolytic fluid into and/or from conduit 14. A valve may be provided in the one or more inlets and/or outlets 15, for shutting off the conduit 14 from the outside. The ends of conduit 14 lie in virtual flat planes, so that they can be substantially closed off by solar cells with a flat planar surface. Electrode 16 is preferably located at substantially equal path lengths to the ends of conduit through the conduit 14.

Solar cells 12a, b may comprise a flat planar semiconductor substrate with parallel surfaces on opposite sides of the substrate. Each of the first and second solar cell 12a,b has one of these surfaces lying against the ends of conduit 14 with the sealing rings 18a, b pressed in between. Conduit 14 may have flanges at its ends, each with a circumferential groove for receiving the sealing rings 18a, b. Although a description is given for use with a solar cell, it will be understood that other planar structures, such as a wafer for integrated circuit production or an integrated circuit die may be used instead. However, use for solar cells is particularly advantageous because it helps to avoid effects of active behavior of the solar cells.

Figure 1A:
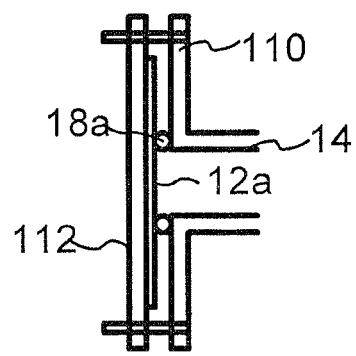
FIG. 1a shows a detail of an embodiment of a measuring device

FIG. 1a shows a detail of an embodiment wherein electrochemical noise measuring device comprises a sample holder, comprising a flange 110 and/or attachment brackets connected to conduit 14 and a solar cell mounting plate 112 attached to flange 110 or brackets. Clamping means may be provide in the form of springs arranged to exert a force between flange 110 or the brackets on one side and mounting plate 112 on the other side in a direction that urges mounting plate 112 towards conduit 14. Alternatively or in addition screws may be provided to exert such a force. In an embodiment such sample holders may be provided at both ends of conduit 14. Although embodiments have been shown wherein two solar cells are used, both pressed to an opening of a conduit, it should be appreciated that more solar cells pressed to different openings to the same mass of electrolytic fluid may be used, or that one of the solar cells may be immersed in the electrolytic fluid, or that one of the solar cells may be replaced by an other reference, such as a conductor plane without underlying solar cell.

Figure 2A:
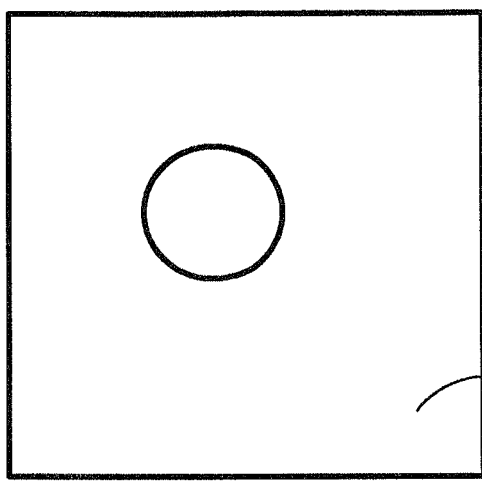
FIG. 2a-c show solar cell surfaces with contact areas
Figure 2B:
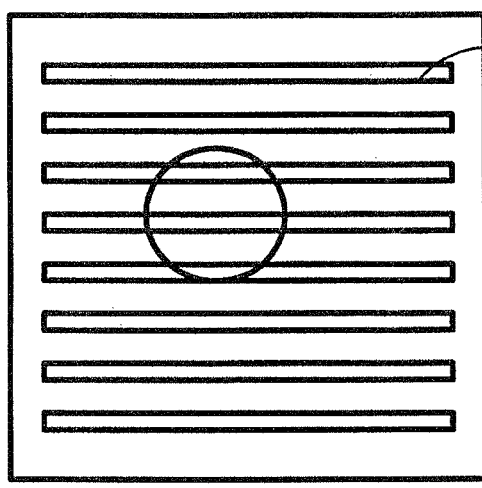
Figure 2C:
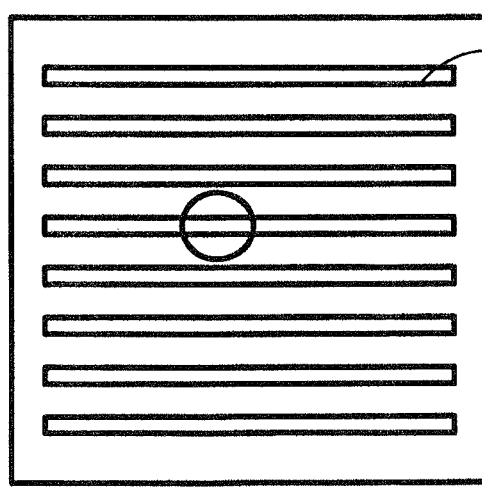

FIGS. 2a-c illustrate a contact area of sealing ring 18a on the surface of first solar cell 12a. As shown in FIG. 2a, first solar cell 12a may have a conductor plane 20 that entirely covers the planar surface facing the end of conduit 14, sealing ring 18a encircling part of conductor plane 20. As shown, conduit 14 may have a circular cross-section, but other cross-sections such as elliptic or polygonal cross sections with correspondingly shaped sealing rings 18a may be used to encircle part of the conductor plane. As used herein "encircling" means running around a closed contour, wherein the contour can have any shape, including a circular shape. As shown in FIG. 2b,c, first solar cell 12a may have pattern of conductor lines 22 (shown lines symbolically) on the planar surface facing the end of conduit 14, sealing ring 18a encircling part of a conductor line. In one embodiment, the diameter of conduit 14 is chosen so that part of only one of the conductor lines 22 is present in the area encircled by sealing ring 18a. In another embodiment, the diameter of conduit 14 is chosen so that parts of plurality of the conductor lines 22 are present in the area encircled by sealing ring 18a. In an embodiment solar cells may be of the metal wrap through type, comprising a conductor in a via between conductors on mutually opposite surfaces of the solar cell. In an embodiment, the exposed area encircled by sealing ring 18a may comprise the end of such a via, in order to test corrosion of the conductor in the via.

In an embodiment partly manufactured solar cells 12a, b are used, wherein the conductors are directly exposed on the surface, without protective layer on top. This provides for direct measurements of corrosion. In another embodiment solar cells 12a, b with a protective electrically insulating layer on the conductors are used. This provides for measurements of the permeability of the protective layer. In a further embodiment part of the conductors in the area encircled by sealing ring 18*a* is directly exposed and part is provided with the protective electrically insulating layer.

Although an embodiment has been shown wherein a straight conduit 14 was used, it will be understood that other shapes may be used. For example, a U-shaped conduit may be used, so that the ends of the conduit are adjacent to each other and solar cells 12*a,b* may be located next to each other. When the legs of the U are turned up, this makes it easier to exchange solar cells 12*a,b* while there is electrolytic fluid in conduit 14. Other shapes may be used, in an embodiment an O shape may be used, wherein the ends of the conduit lie against mutually opposite surface of a single same solar cell. Conduit 14 need not be rigid. In an embodiment a flexible conduit may be used.

In operation, electrolyte fluid in conduit 14 is in contact with the surface of solar cells 12*a,b* in the area encircled by sealing ring 18*a*. In an embodiment, the electrolyte fluid may comprise acetic acid solution of less than 0.1 M (mimicking acetatic acid that is excreted from solar cell encapsulant), a soldering flux diluted in water, water containing Na+ ions, artificial rain water or a combination thereof. The first terminal of electronic measuring circuit 19 is electrically connected to electrode 16 and the second and third terminals are in contact with the conductor planes 20 or one or more conductor lines 22 on the surfaces of first and second sample solar cell 12*a,b* respectively. The contact to the conductor planes 20 or one or more conductor lines 22 is made on the surface of the solar cells outside the areas encircled by sealing rings 18*a, b*.

In an embodiment, a process may be used wherein a protective electrically insulating layer is provided on the exposed area and subsequently a scratch is made in the protective electrically insulating layer to expose the exposed area before the solar cell 12*a,b* is brought into contact with the electrolytic fluid. This makes it possible to measure the effect of scratches on corrosion.

Figure 3:
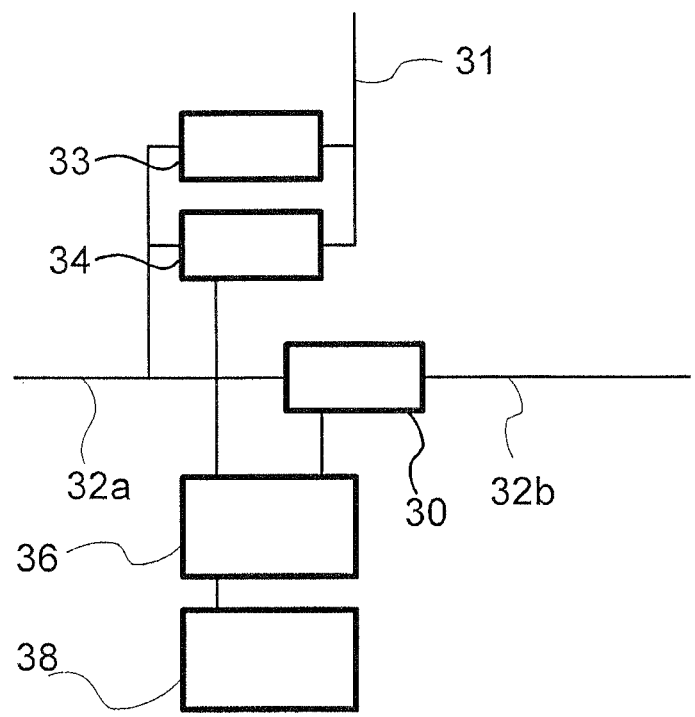
FIG. 3 shows an electronic measuring circuit.

FIG. 3 shows an embodiment of electronic measuring circuit 19 comprising a short circuit current sensor 30 coupled between the second and third terminals 32*a,b*, a voltage sensor 34 coupled between the first terminal 31 and the second terminal 32*a*. In an embodiment, voltage sensor 34 is DC-decoupled from second terminal 32*a*, e.g. by a capacitor (not shown). The electronic measuring circuit 19 comprises a memory 36 coupled to short circuit current sensor 30 and voltage sensor 34 and a data processor 38 coupled to memory 36. In operation short circuit current sensor 30 and voltage sensor 34 sense current and voltages at successive time points and store digitized results in memory 36. The sensors may comprise a one or more digital to analog converters. Optionally, data processor 38 may act as an intermediate between current sensor 30 and voltage sensor 34 on one hand and memory 36 on the other hand for said storing. Optional voltage source 33 will be discussed further on.

Data processor 38 may comprise a program for causing data processor 38 to compute and optionally display various parameters derived from the measured voltages and currents that are indicative of corrosion processes. As used herein, the presence of such a program will be indicated by stating that data processor 38 is configured to execute the relevant computations, or simply by stating that data processor 38 does so. The program may be provided on a tangible computer readable medium such as on a magnetic or optical disk, or a (non-volatile) semi-conductor memory or transmitted to data processor as a signal. Data processor 38 may be a multi-processor system, comprising a plurality of programmable processing circuits.

At least initially corrosion at the interface between a conductor on the solar cell and the electrolyte fluid proceeds by means of local chemical reaction events that involve charge transfer between the conductor and the electrolyte fluid. Hence such reaction events give rise to current and/or voltage fluctuations in electric circuits that comprise the interface. Other events at the interface that give rise to current and/or voltage fluctuations in such an electric circuit include sudden film rupture, crack propagation, and hydrogen discharge with gas bubble formation and detachment. The current and voltage fluctuations in such an electric circuit are a sum of contributions of such events. The standard deviations of the current and voltage fluctuations can be used in a measure for the rate of corrosion. For example, the electrochemical noise resistance may be computed as a ratio between the standard deviations of the voltage and the current. As another example, a ratio between the power spectral densities (PSD) of the voltage and current fluctuations as a function of frequency may be used. The PSD may be computed for example by taking the square of the absolute value of the Fourier transform of a series of values of the voltage.

In an embodiment, data processor 38 is configured to compute estimates of linear trends in the voltage and current measurements from sensors 30, 34, to subtract this trend and to compute standard deviations and/or PSDs from the results of the subtraction. Furthermore data processor 38 may be configured to compute ratios of the standard deviations and/or PSDs obtained from the voltage and current measurements from sensors 30, 34.

These and other forms of electrochemical noise measurements are known per se, for example from "Electrochemical noise analysis (ENA) for active and passive systems in chloride media" by Mansfels et al. Electrochimica Acta 46 (2001) 3651-3664, "On the interpretation of the electrochemical noise data for coatings" Greisiger et al. Progress in Organic Coatings 39 (2000) 31-36 and "R/S fractal analysis of electrochemical noise signals of three organic coating samples under corrosion conditions" Gonzalez-Nunez et al. Journal of Corrosion Science and Engineering, Volume 6, Paper C117, From the PSD data processor 38 may compute the spectral noise impedance at lowest frequency e.g. by extrapolating PSD values from non-zero frequencies or from an average of lowest N measured frequencies, where N=10 for example). Furthermore data processor 38 may compute the slope of the PSD of voltage or current fluctuations as a function of frequency for use as an indication of the mode of corrosion, and the ratio of the voltage and current PSDs (or its square root).

Alternatively, or in addition data processor 38 may compute time domain parameters such as the mean value of potential (voltage) and current fluctuations, their standard deviation, the noise resistance (the ratio of the standard deviation of voltage and current fluctuations), the skewness of potential and current fluctuations (the average cube of deviations from the mean value), the kurtosis of potential and current fluctuations (the average fourth power of deviations from the mean value), the Hurst exponent of the fluctuations of current and potential (ratio of logarithms of), which describes the roughness of the time series and the characteristics of the corrosion process, and the mean square of the current noise, which provides kinetic information about the corrosion process.

Electrochemical noise measuring device 10 may comprise a temperature control device for controlling the temperature of the electrolytic fluid. The temperature control device may comprise a heater in conduit 14 or in a sheet on the surface of conduit, a temperature sensor in thermal contact with the space for the electrolytic fluid and a controller in a temperature feedback loop.

Electrochemical noise measuring device 10 may comprise a stirring device for stirring the electrolytic fluid. A magnet may be provided in conduit 14 and a rotating magnetic field generator outside conduit for example. In another embodiment a motor driven fan may be provided in conduit 14.

Measurement Configurations

Electronic measuring circuit 19 may be configured to perform a number of different types of measurement.

In a simple measurement, electronic measuring circuit 19 determines current values of current through a short circuit between the second and third terminals as a function of time, i.e. currents through a circuit that contains the electrolyte fluid, the conductors on the surface of the solar cells and the short circuit. In another simple measurement, electronic measuring circuit 19 determines voltage difference between the second and third terminals as a function of time, i.e. voltage differences between conductors on the surface of the solar cells that are connected via the electrolyte fluid. Data processor 38 may compute standard deviations and/or PSDs and/or other parameters from current values and from these voltage values. For these simple measurements, electrode 16 could be omitted from conduit 14.

In other measurements electronic measuring circuit 19 may be configured to perform simultaneous measurements of short circuit current between the second and third terminals and voltage differences between the first terminal and the second and/or third terminal. Data processor 38 may compute standard deviations and/or PSDs and/or other parameters from current values and from these voltage values.

In an embodiment, solar cells 12*a,b* of the same type may be used at both ends of conduit 14, i.e. cells with conductors of the same material and in the same pattern. In another embodiment, solar cells 12*a,b* of the mutually different type may be used at the ends of conduit 14. Usually, different surfaces can be distinguished in a solar cell, such as an emitter surface, a doped layer that gives rise to a semiconductor junction with the main body of the solar cell lying near the emitter surface, and a base surface having no junction but optionally a surface field layer with enhanced doping. In an embodiment, solar cells 12*a,b* have the same type of surface (emitter-emitter or base-base) with conductors thereon facing the ends of conduit 14. In an embodiment, solar cells 12*a,b* have different types of surface (base-emitter) with conductors thereon facing the ends of conduit 14.

For use in an embodiment wherein solar cells 12*a,b* of the same type are used at both ends of conduit 14, or different types of surface of the same type of cell, data processor 38 may be configured to determine asymmetry in the noise signals to detect which solar cell or surface 12*a,b* suffers most from corrosion. Asymmetry may be determined by computing values of a statistical property from positive and negative current and/or voltage fluctuations respectively (deviations from the average with positive and negative sign). Data processor 38 may be configured to determine the amplitude distribution of positive and negative fluctuation peaks in the voltage and/or current, PSD's of the positive and negative fluctuation peaks, or average amplitudes of positive and negative fluctuation peaks for example. The values of such a statistical property for positive and negative fluctuations may be compared directly, or by computing their difference.

FIG. 3 shows that electronic measuring circuit 19 may additionally comprise a voltage source 33 (for generating high voltages in a range of 100V-3 kV), is provided parallel to voltage sensor 34, to apply a bias voltage during current measurements. Voltage source 33 with a high frequency blocking circuit may be used that has sufficiently high impedance for fluctuations in a measurement range of voltage sensor 34 to allow such fluctuations.

In an embodiment first terminal 31 of electronic measuring circuit 19 is coupled to ground (e.g. to an external ground connection, not shown and/or to a housing of electronic measuring circuit 19). This means that second and third electrodes 33*a,b* will be at high potential relative the ground, as well as the conductors on the solar cells 12*a,b*. Electrode 16 may be used to mount the device on a mechanical support. This provides for a simple design, because the electrically insulating material of conduit 14 provides for a safe suspension of the solar cells 12*a,b*.

Voltage source 33 can be used to simulate the effect of series connection of a plurality of solar cells, in order to obtain measurements of corrosion in a series connection of a plurality of solar cells. Although an embodiment has been shown wherein voltage source is coupled to the same contact on solar cell 12*a* and to the same electrode 16 that are used for measurements, it should be understood that voltage source 33 may instead be connected via a further electrode in the electrolytic fluid and/or a further contact on the conductor layer on solar cell 12*a*.

In an embodiment the planar surface of the solar cell 12*a,b* opposite to the planer surface with the exposed area is kept in the dark during the measurements. A cover sheet may be provided on the opposite planar surface for example. Thus, effects of photo-voltages can be avoided.

In an embodiment a conduit of optically transparent material is used, which passes light in the visual and/or near infrared wavelength range.

Figure 4:
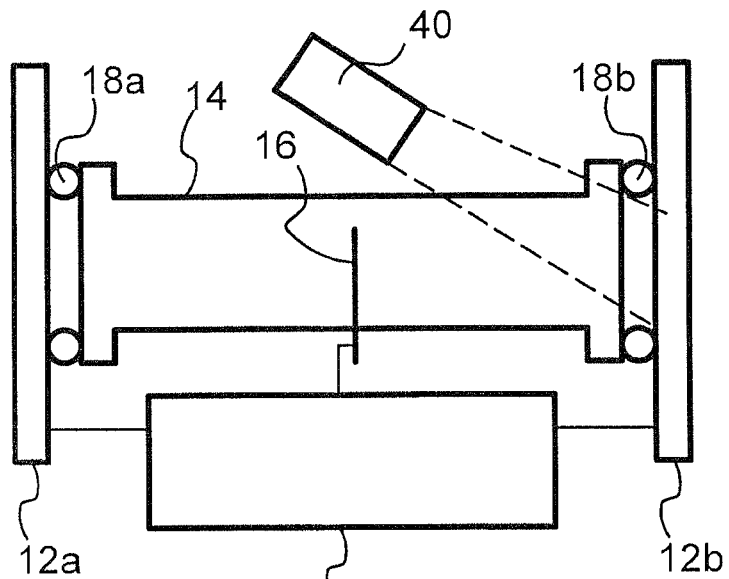
FIG. 4, 5 show embodiments of an electrochemical noise measuring device

FIG. 4 shows an embodiment of the electrochemical noise measuring device 10 that comprises a light source 40 directed through conduit at one of the ends of conduit 14. The data processor (not shown) may have an output coupled to a control input of light source 40.

In this embodiment measurements may performed in an environment wherein the area of a first one of solar cells 12*a,b* that is exposed to the electrolyte fluid in conduit 14 is irradiated with light through the wall of conduit 14. From these measurements, the effect of lighting on corrosion can be determined. In the measurements, the area that is exposed to the electrolytic fluid in the other one of the solar cells 12*a,b* may be kept dark, or at least subject to irradiation of less intensity, to obtain measurements that depend on the difference of lighting conditions. In an embodiment intensities that are different only in a predetermined wavelength range are used, e.g. by placing a color filter between a light source and one of the solar cells 12*a,b* only.

The data processor may be configured to vary the light intensity produced by light source 40 e.g. by switching it on and off in respective time intervals, or by switching between different intensities, or continuously varying the intensity and to determine noise parameters such as voltage and current standard deviations and PSDs in synchronism with the variations.

As used herein, determining the noise parameters in synchronism with variation in light intensity covers determining a correlation between variations of the noise parameters obtained from the measurements and the variation of the light intensity. For example, performing respective measurements in time intervals wherein first and second different irradiation intensities are used respectively (e.g. zero and non-zero intensity) and extracting noise parameters obtained from the measurements performed in the intervals with different intensity. Data processor 38 may be configured to extract these noise parameters separately for the time intervals with different intensity. In an embodiment data processor 38 may be configured to subtract the noise parameters obtained from the intervals with different intensity.

When periodically alternating intervals are used, determination in synchronism may cover averaging noise parameters obtained for intervals with corresponding intensity. When continuous variations are used, a product of the intensity variations as a function of time and noise parameters as a function of time may be computed and averaged.

In another embodiment, a light source or light source for lighting the areas exposed to electrolytic fluid with equal intensity are provided. This makes it possible to compare corrosion of different types of solar cell 12a,b under the same lighting conditions. The data processor may be configured to determine noise parameters such as voltage and current standard deviations and PSDs in synchronism with lighting variations. From these measurements, the effect of lighting on different modes of corrosion can be determined.

In another embodiment the electrochemical noise measuring device 10 may comprise a light source or light sources placed at locations to light the back of the cells. The data processor may have an output coupled to a control input of this light source or these light sources. This makes it possible to compare corrosion of different types of solar cell 12a,b dependent on electrovoltaic voltages or currents generated by the light.

Figure 5:
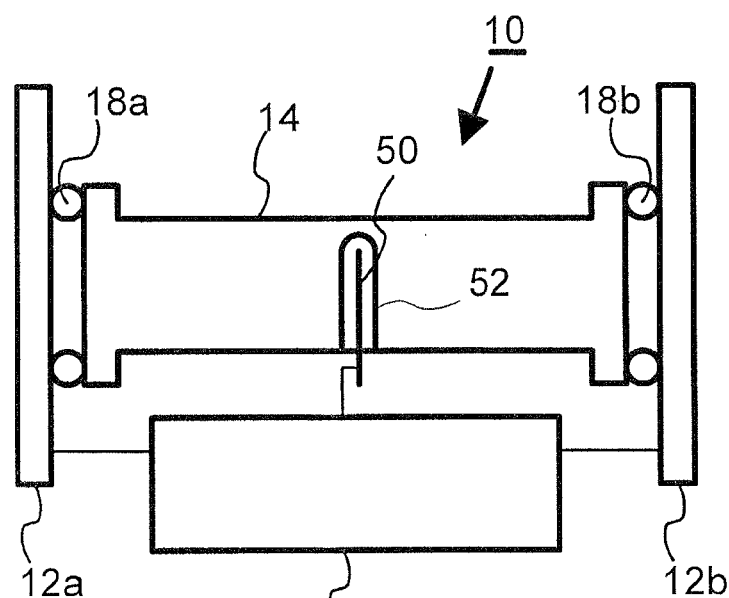

FIG. 5 shows an embodiment of an electrochemical noise measuring device 10 wherein an electrode 50 covered with a glass layer 52 is used, so that glass layer 52 separates electrode 50 from the electrolyte fluid in conduit 14. Glass layer 52 may be used to simulate the effect of a glass packaging of the solar cells when to obtain measurements of corrosion in a series connection of a plurality of solar cells is used.

The invention claimed is:

1. A method of measuring corrosion effects in a solar cell, the method comprising
    keeping a planar surface of the solar cell and a rim of an open end of a conduit directly or indirectly pressed against each other, the conduit comprising electrolytic fluid, whereby an exposed area of the solar cell that is encircled by the open end of the conduit is exposed to the electrolytic fluid, leaving a free part of the planar surface of the solar cell extending beyond said exposed area unexposed;
    measuring current and/or voltage fluctuations in an electric circuit that contains the electrolytic fluid, an interface between the electrolytic fluid on the exposed area and a conductor layer on the planar surface, and a contact to the conductor layer.

2. A method according to claim 1, wherein the step of measuring current and/or voltage fluctuations comprises measuring fluctuations of a voltage between the contact and an electrode in the electrolytic fluid.

3. A method according to claim 1, comprising applying a bias voltage between the contact or a further contact on the conductor layer and an electrode in the electrolytic fluid.

4. A method according to claim 3, wherein the electrode in the electrolytic fluid is covered with a glass layer.

5. A method according to claim 1, wherein the conduit is at least locally optically transparent, the method comprising irradiating the planar surface in the exposed area with light through the conduit during at least part of said measuring of current and/or voltage fluctuations.

6. A method according to claim 5, comprising varying an intensity of the light, and determining results from the measurements of the current and/or voltage fluctuations in synchronism with variation of the light intensity.

7. A method according to claim 1, comprising irradiating a further planar surface of the solar cell that is parallel to the planar surface during at least part of said measuring of current and/or voltage fluctuations.

8. A method according to claim 1, comprising varying a temperature of the solar cell and determining results from the measurements of the current and/or voltage fluctuations in synchronism with variation of the temperature.

9. A method according to claim 1, comprising keeping a further planar surface of a further solar cell and a further open end of a conduit directly or indirectly pressed against each other, whereby a further exposed area of the further solar cell is exposed to the electrolytic fluid, leaving a further free part of the further planar surface extending beyond said further exposed area unexposed; and wherein the electric circuit contains a further conductor layer on the further planar surface, a further contact to said further conductor layer in said further free part and an interface between the further conductor layer and the electrolytic fluid in said further exposed area.

10. A method according to claim 9, wherein the conduit is at least locally optically transparent, the method comprising irradiating the planar surface in the exposed area and the further exposed area with light of equal intensity during at least part of said measuring of current and/or voltage fluctuations.

11. A method according to claim 1, wherein at least the conductor layer on said exposed area is covered by a protective electrically insulating layer, and wherein a scratch is made in the protective electrically insulating layer on the exposed area before the planar surface and the open end are pressed against each other.

12. A measuring system for measuring corrosion effects in a solar cell, the system comprising
    a conduit comprising electrolytic fluid;
    a solar cell having a planar surface, the solar cell comprising a conductor layer on the planar surface and a contact to the conductor layer, a rim of the conduit at an open end of the conduit being directly or indirectly in contact with the planar surface, whereby an exposed area of the solar cell that is encircled by the open end of the conduit is exposed to the electrolytic fluid, leaving a free part of the planar surface of the solar cell extending beyond said exposed area unexposed;
    an electric measuring device with a first terminal connected to the contact and a second terminal coupled to the electrolytic fluid in the conduit, the electric measuring device being configured to measure current and/or voltage fluctuations between the first and second terminal.

13. A measuring system according to claim 12, comprising an electrode in the conduit and connected to the second terminal.

14. A measuring system according to claim 12, comprising a voltage source and an electrode in the electrolytic fluid, the voltage source being coupled between the contact or a further contact on the conductor layer and the electrode connected to the second terminal.

15. A measuring system according to claim 14, wherein the electrode in the electrolytic fluid is covered by a glass layer.

16. A measuring system according to claim 12, wherein the conduit is at least locally optically transparent, the system comprising a light source directed to irradiate the exposed area through the conduit.

17. A measuring system according to claim 16, wherein the measuring device is configured to cause the light source to vary an intensity of the irradiating light and to measure said current and/or voltage fluctuations in synchronism with variation of the intensity.

18. A measuring system according to claim 12, comprising a light source directed at a further planar surface of the solar cell, the further planar surface being parallel to said planar surface.

19. A measuring system according to claim 12, comprising a temperature adjusting element thermally coupled to the solar cell.

20. A measuring system according to claim 19, comprising an electrode in the conduit, the electric measuring device having a third terminal connected to the electrode.

* * * * *